(12) United States Patent
Norman et al.

(10) Patent No.: US 10,065,180 B2
(45) Date of Patent: *Sep. 4, 2018

(54) PROCESS FOR PREPARING MODIFIED V—TI—P CATALYSTS FOR SYNTHESIS OF 2,3-UNSATURATED CARBOXYLIC ACIDS

(71) Applicant: Eastman Chemical Company, Kingsport, TN (US)

(72) Inventors: David William Norman, Kingsport, TN (US); Greg Alan King, Mount Carmel, TN (US)

(73) Assignee: Eastman Chemical Company, Kingsport, TN (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/829,245

(22) Filed: Dec. 1, 2017

(65) Prior Publication Data

US 2018/0078927 A1  Mar. 22, 2018

Related U.S. Application Data

(60) Division of application No. 14/509,517, filed on Oct. 8, 2014, now Pat. No. 9,861,965, which is a continuation of application No. 13/234,323, filed on Sep. 16, 2011, now Pat. No. 8,883,672.

(51) Int. Cl.

| | | |
|---|---|---|
| *C07B 35/00* | (2006.01) |
| *B01J 27/199* | (2006.01) |
| *B01J 37/08* | (2006.01) |
| *B01J 21/06* | (2006.01) |
| *B01J 23/00* | (2006.01) |
| *C07C 51/353* | (2006.01) |
| *C07C 57/04* | (2006.01) |
| *B01J 27/198* | (2006.01) |
| *B01J 37/03* | (2006.01) |
| *B01J 35/00* | (2006.01) |

(52) U.S. Cl.
CPC .......... *B01J 27/199* (2013.01); *B01J 21/063* (2013.01); *B01J 23/002* (2013.01); *B01J 27/198* (2013.01); *B01J 37/03* (2013.01); *B01J 37/086* (2013.01); *C07C 51/353* (2013.01); *C07C 57/04* (2013.01); *B01J 35/002* (2013.01); *B01J 2523/00* (2013.01); *B01J 2523/13* (2013.01); *B01J 2523/47* (2013.01); *B01J 2523/51* (2013.01); *B01J 2523/55* (2013.01)

(58) Field of Classification Search
CPC ...................................................... B01J 27/199
USPC ....................................................... 562/599
See application file for complete search history.

(56) References Cited

U.S. PATENT DOCUMENTS

| | | |
|---|---|---|
| 3,086,026 A | 4/1963 | Wiebusch |
| 3,226,337 A | 12/1965 | Riemenschneider et al. |
| 3,657,331 A | 4/1972 | Ackermann et al. |
| 3,684,741 A | 8/1972 | Friedrichsen et al. |
| 3,894,971 A | 7/1975 | Reuter et al. |
| 3,926,846 A | 12/1975 | Ono et al. |
| 3,933,888 A | 1/1976 | Schlaefer |
| 4,040,913 A | 8/1977 | Clovis et al. |
| 4,085,143 A | 4/1978 | Holmes |
| 4,092,332 A | 5/1978 | Freerks et al. |
| 4,151,116 A | 4/1979 | McDermott |
| 4,165,438 A | 8/1979 | Schneider |
| 4,177,161 A | 12/1979 | Umemura et al. |
| 4,276,197 A | 6/1981 | Vartuli et al. |
| 4,312,787 A | 1/1982 | Dolhyj et al. |
| 4,333,858 A | 6/1982 | Decker et al. |
| 4,339,598 A | 7/1982 | Guttmann et al. |
| 4,382,876 A | 5/1983 | Neubold et al. |
| 4,447,638 A | 5/1984 | Gaffney et al. |
| 4,490,476 A | 12/1984 | Piccolini et al. |
| 4,515,904 A | 5/1985 | Edwards |
| 4,581,471 A | 4/1986 | Barlow et al. |
| 4,599,144 A | 7/1986 | Baleiko et al. |
| 4,677,225 A | 6/1987 | Niizuma et al. |
| 4,736,062 A | 4/1988 | Hagen et al. |
| 4,743,706 A | 5/1988 | Guttmann et al. |
| 4,784,981 A | 11/1988 | Alpers et al. |
| 4,801,571 A | 1/1989 | Montag et al. |
| 4,942,258 A | 7/1990 | Smith |
| 4,943,659 A | 7/1990 | Hagen |
| 4,973,569 A | 11/1990 | Bowman et al. |

(Continued)

FOREIGN PATENT DOCUMENTS

| | | |
|---|---|---|
| CN | 1106315 A | 8/1995 |
| DE | 1294956 | 5/1969 |

(Continued)

OTHER PUBLICATIONS

Abon, M., et al.; "Evolution of a VPO Catalyst in n-Butane Oxidation Reaction during the Activation Time"; Journal of Catalysis; 1995; pp. 28-36; vol. 156; Academic Press, Inc.

(Continued)

*Primary Examiner* — Deborah D Carr

(74) *Attorney, Agent, or Firm* — James Arnold, Jr.

(57) ABSTRACT

The invention relates to a catalyst composition comprising a mixed oxide of vanadium, titanium, and phosphorus modified with alkali metal. The titanium component is derived from a water-soluble, redox-active organo-titanium compound. The catalyst composition is highly effective at facilitating the vapor-phase condensation of formaldehyde with acetic acid to generate acrylic acid, particularly using an industrially relevant aqueous liquid feed.

7 Claims, 5 Drawing Sheets

(56) References Cited

U.S. PATENT DOCUMENTS

| | | |
|---|---|---|
| 4,990,662 A | 2/1991 | Hagen et al. |
| 5,039,644 A | 8/1991 | Lachman et al. |
| 5,169,820 A | 12/1992 | Ueda et al. |
| 5,241,114 A | 8/1993 | Smith et al. |
| 5,496,787 A | 3/1996 | Hatano et al. |
| 5,506,187 A | 4/1996 | Haddad et al. |
| 5,710,328 A | 1/1998 | Spivey et al. |
| 5,792,722 A | 8/1998 | Haddad et al. |
| 5,808,148 A | 9/1998 | Gogate et al. |
| 5,877,330 A | 3/1999 | Kishimoto et al. |
| 5,932,746 A | 8/1999 | Herron et al. |
| 5,998,657 A | 12/1999 | Gogate et al. |
| 6,265,618 B1 | 7/2001 | Zoeller et al. |
| 6,329,549 B1 | 12/2001 | Waller et al. |
| 6,429,332 B1 | 8/2002 | Tanimoto et al. |
| 6,525,216 B1 | 2/2003 | Nishimura et al. |
| 6,652,823 B2 | 11/2003 | Teunissen |
| 6,670,501 B1 | 12/2003 | Harrison et al. |
| 6,812,351 B2 | 11/2004 | Weiguny et al. |
| 6,858,561 B2 | 2/2005 | Bortinger et al. |
| 6,903,047 B2 | 6/2005 | Kourtakis et al. |
| 6,956,004 B2 | 10/2005 | Albonetti et al. |
| 7,015,357 B2 | 3/2006 | Yada et al. |
| 7,060,649 B2 | 6/2006 | Weiguny et al. |
| 7,157,599 B2 | 1/2007 | Goto et al. |
| 7,547,655 B2 | 6/2009 | Lan |
| 7,638,457 B2 | 12/2009 | Ghelfi et al. |
| 8,883,672 B2 * | 11/2014 | Norman ............... B01J 37/03 502/209 |
| 2002/0183199 A1 | 12/2002 | Bogan, Jr. |
| 2004/0006244 A1 | 1/2004 | Manzer |
| 2004/0014990 A1 | 1/2004 | Storck et al. |
| 2004/0162217 A1 | 8/2004 | Albonetti et al. |
| 2004/0241067 A1 | 12/2004 | Oki et al. |
| 2005/0137422 A1 | 6/2005 | Hazin et al. |
| 2009/0209665 A1 | 8/2009 | Fu et al. |
| 2010/0016644 A1 | 1/2010 | Forkner |
| 2010/0069650 A1 | 3/2010 | Hibst et al. |
| 2010/0076233 A1 | 3/2010 | Cortright et al. |
| 2010/0087663 A1 | 4/2010 | Hibst et al. |
| 2010/0105926 A1 | 4/2010 | Hibst et al. |
| 2010/0105927 A1 | 4/2010 | Hibst et al. |
| 2011/0213174 A1 | 9/2011 | Dubois |
| 2012/0071687 A1 | 3/2012 | Herzog et al. |
| 2012/0071688 A1 | 3/2012 | Herzog et al. |
| 2012/0277466 A1 | 11/2012 | Nagaki et al. |
| 2012/0289743 A1 | 11/2012 | Nagaki et al. |
| 2013/0072696 A1 | 3/2013 | Norman |
| 2013/0102455 A1 | 4/2013 | Haddad et al. |
| 2013/0237724 A1 | 9/2013 | Boppana et al. |

FOREIGN PATENT DOCUMENTS

| | | |
|---|---|---|
| DE | 102004014932 A1 | 10/2004 |
| EP | 0147156 B1 | 8/1988 |
| EP | 2135671 A2 | 12/2009 |
| EP | 2340888 A1 | 7/2011 |
| GB | 1462724 A | 1/1977 |
| JP | 48-049736 B2 | 7/1973 |
| JP | S57-144039 A | 9/1982 |
| JP | 58-151313 | 9/1983 |
| JP | 58-188834 A | 11/1983 |
| JP | 61-229840 A | 10/1986 |
| JP | 64-066141 A | 3/1989 |
| JP | 64-068334 A | 3/1989 |
| JP | 64-068335 A | 3/1989 |
| JP | 64-068336 | 3/1989 |
| JP | 64-068337 A | 3/1989 |
| JP | 05-017392 A | 1/1993 |
| JP | 1996-259494 A | 10/1996 |
| JP | 2003-326168 | 11/2003 |
| JP | 2010-254887 A | 11/2010 |
| RO | 114084 B1 | 1/1999 |
| RO | 117512 B1 | 4/2002 |
| WO | WO 2006/072447 A1 | 7/2006 |
| WO | WO 2010-046227 A1 | 4/2010 |
| WO | WO 2012/148837 A1 | 11/2012 |
| WO | WO 2012/154396 A1 | 11/2012 |

OTHER PUBLICATIONS

Al, Mamoru; "Vapor-Phase Aldol Condensation of Formaldehyde with Propionic Acid on Vanadium Pentoxide—Phosphorus Pentoxide"; Applied Catalysis; 1988; pp. 221-330; vol. 36; Elsevier Science Publishers; The Netherlands.

Al, M.; "Preparation of High-Surface-Area Titanium-Vanadium Binary Pyrophosphate Catalysts"; Applied Catalysis; 1989; pp. 51-61; vol. 48; Elsevier Science Publishers; The Netherlands.

Al, Mamoru; "Effect of the Composition of Vanadium-Titanium Binary Phosphate on Catalytic Performance in Vapor-Phase Aldol Condensation"; Applied Catalysis; 1989; pp. 29-36; vol. 54; Elsevier Science Publishers; The Netherlands.

Al, Mamoru; "Reaction of Acetic Acid with Methanol over Vanadium-Titanium Binary Phosphate Catalysts in the Presence of Oxygen"; Applied Catalysis; 1990; pp. 227-235; vol. 59; Elsevier Science Publishers; The Netherlands.

Al, Mamoru; "Reaction of Propionic Acid with Methylal Over Vanadium-Silicon-Phosphorus Oxide"; Applied Catalysis; 1990; pp. 365-373; vol. 63; Elsevier Science Publishers; The Netherlands.

Al, Mamoru, et al.; "Production of methacrylic acid by vapor-phase aldol condensation of propionic acid with formaldehyde over silica-supported metal phosphate catalysts"; Applied Catalysis A: General; 2003; pp. 185-191; vol. 252; Elsevier.

Al, Mamoru; "Formation of methyl methacrylate by condensation of methyl propionate with formaldehyde over silica-supported cesium hydroxide catalysts"; Applied Catalysis A: General; 2005; pp. 211-215; Elsevier.

Al, Mamoru; "The Effects of the Reaction Variables on the Yields of Acrylic Acid and Methyl Acrylate in the Reaction of Acetic Acid with Methanol in the Presence of Oxygen"; Bulletin Chemical Society Japan; Jan. 1990; pp. 199-202; vol. 63, No. 1; The Chemical Society of Japan.

Al, Mamoru; "The Production of Methacrylic Acid by the Vapor-Phase Aldol Condensation over V—Si—P Ternary Oxide Catalyst"; Bulletin Chemical Society Japan; Apr. 1990; pp. 1217-1220; vol. 63, No. 4; The Chemical Society of Japan.

Al, Mamoru; "Reaction of Methyl Propionate with Methylal over V—Si—P Ternary Oxide Catalysts"; Bulletin Chemical Society Japan; Dec. 1990; pp. 3722-3724; vol. 63, No. 12; The Chemical Society of Japan.

Al, Mamoru; "Formation of Acrylaldehyde by Vapor-Phase Aldol Condensation II. Phosphate Catalysts"; Bulletin Chemical Society Japan; Apr. 1991; pp. 1346-1350; vol. 64, No. 4; The Chemical Society of Japan.

Al, M..; "Chapter 5. Vapor Phase Condensation Reactions Using Formaldehyde or Methanol"; Catalysis; 1996; pp. 152-198; vol. 12; The Royal Society of Chemistry.

Al, Mamoru; "Formation of methyl methacrylate from methyl propionate and methanol"; Catalysis Today; 2006; pp. 398-402; vol. 111; Elsevier.

Al, Mamoru; "Vapor-Phase Aldol Condensation of Formaldehyde with Acetic Acid on $V_2O_5$—$P_2O_5$ Catalysts"; Journal of Catalysis; Apr. 1987; pp. 201-208; vol. 107; Academic Press.

Al, Mamoru: "Vapor-Phase Reaction of Methanol with Methyl Acetate and Acetic Acid in the Presence of Oxygen"; Journal of Catalysis; Feb. 1988; pp. 194-200; vol. 112; Academic Press.

Al, Mamoru; "Effects of Organic Compounds Used in Preparing V/Ti Binary Phosphate Catalysts"; Journal of Catalysis; 1988; pp. 562-566; vol. 113; Academic Press, Inc.

Al, Mamoru; "The Production of Methacrylic Acid by the Vapor-Phase Aldol Condensation of Propionic Acid with Formaldehyde"; Journal of Catalysis; 1990; pp. 293-296; vol. 124; Academic Press, Inc.

Al, Mamoru; "Comparison of catalytic properties for partial oxidation between heteropolyacids and phosphates of vanadium and iron"; Journal of Molecular Catalysis A: Chemical; 1996; pp. 3-13; vol. 114; Elsevier.

(56) References Cited

OTHER PUBLICATIONS

Al, Mamoru; "Catalytic Activity for Vapor-Phase Aldol Condensation and Acid-Base Properties of Metal-Oxide Catalysts"; New Frontiers in Catalysis; Jul. 1992; pp. 1199-1210; Elsevier Science Publishers B.V.
Al, Mamoru; "Vapor-Phase Aldol Condensation of Formaldehyde with Acetic Acid, Propionic Acid, and their Derivatives on $(VO)_2P_2O_7$—$TiP_2O_7$ Catalysts"; Proc. $9^{th}$ Intern. Congress on Catalysis; 1988; pp. 1562-1569; Canada, Ottawa.
Al, Mamoru; "Preparation of high surface area titanium-vanadium binary pyrophosphate catalysts"; Shokubai; 1988; pp. 420-423 (abstract only); vol. 30, No. 6.
Al, M.; "Reaction of Methyl Acetate with Methylal in the Presence of Oxygen"; Studies in Surface Science and Catalysis; 1992; pp. 101-108; vol. 72; Elsevier Science Publishers B. V.
Bartley, Jonathan K., et al.; "Chapter 12. Vanadium Phosphate Catalysts"; Metal Oxide Catalysis; 2009; pp. 499-537; WILEY-VCH Verlag GmbH & Co. KgaA; Weinheim.
Bish, D. L. and Howard, S. A.; "Quantitative Phase Analysis Using the Rietveld Method"; Journal of Applied Crystallography; 1988; pp. 86-91; vol. 21; International Union of Crystallography.
Marcu, Ioan-Cezar, et al.; "Effects of the method of preparing titanium pyrophosphate catalyst on the structure and catalytic activity in oxidative dehydrogenation of n-butane"; Journal of Molecular Catalysis A; Chemical; Apr. 2003; pp. 241-250; vol. 203; Elsevier.
Murthy, N.S, et al., "General procedure for evaluating amorphous scattering and crystallinity from X-ray diffraction scans of semicrystalline polymers". H. Polymers; 1990; pp. 996-1002; vol. 31.
"Nitrogen" in Kirk-Othmer Encyclopedia of Chemical Technology, Published Online: May 13, 2005, Copyright © 2001 by John Wiley & Sons, Inc. pp. 1-23.
Otake, Masayuki; "Method for the Manufacture of Composite Oxide Catalyst"; English translation of JP S64-4817, Publication Date is Jan. 26, 1989.
Rietveld, H. M.; "A profile refinement method for nuclear and magnetic structures"; Journal of Applied Crystallography; Jun. 1969; pp. 65-71; vol. 2, Part 2 (Abstract).
Scherrer, P.; "Bestimmung der Grösse und der inneren Struktur von Kolloidteilchen mittels Röntgenstrahlen"; Nachrichten von der Königlichen Gesellschaft der Wissenschaften zu Göttingen; Jahre 1918; pp. 98-100.
Tong, Xin et al.; "Photocatalytic Activity of TiOx with Micrometer-Sized Macropores"; Acta Physico-Chimica Sinica (Wuli Huaxue Xuebao), 27 (8); 2011; pp. 1941-1946 (English Abstract).
Yoshitake, Hideaki and Tatumi, Takashi; "Vandium Oxide Incorporated into Mesoporous Titania with a BET Surface Area above 1000 $m^2.g^{-1}$: Preparation, Spectroscopic Characterization and Catalytic Oxidation"; Chemistry of Materials; Feb. 2003; pp. 1695-1702; vol. 15; American Chemical Society.
U.S. Appl. No. 13/234,313, filed Sep. 16, 2011; now U.S. Pat. No. 8,765,629; Norman et al.
U.S. Appl. No. 13/826,180, filed Mar. 14, 2013; now U.S. Pat. No. 8,993,801; Boppana et al.
Co-pending U.S. Appl. No. 14/626,111, filed Feb. 19, 2015; now U.S. Pat. No. 9,493,390; Boppana et al.
Co-pending U.S. Appl. No. 14/859,751, filed Sep. 21, 2015; Deng et al.; now U.S. Pat. No. 9,573,119.
U.S. Appl. No. 13/234,277, filed Sep. 16, 2011; now U.S. Pat. No. 8,981,172; Norman.
Notification of Transmittal of the International Search Report and the Written Opinion of the International Searching Authority, or the Declaration dated Jan. 2, 2013 received in corresponding International Application No. PCT/US2012/053359.
Notification of Transmittal of the International Search Report and the Written Opinion of the International Searching Authority, or the Declaration dated Jan. 2, 2013 received in corresponding International Application No. PCT/US2012/052989.
Notification of Transmittal of the International Search Report and the Written Opinion of the International Searching Authority, or the Declaration dated Dec. 11, 2012 received in corresponding International Application No. PCT/US2012/053365.

* cited by examiner

X-ray diffraction pattern of the 2.5 wt% potassium V-Ti-P catalyst prepared in Example 1.

X-ray diffraction pattern of the unmodified V-Ti-P catalyst prepared in Comparative Example 1.

X-ray diffraction pattern of the 9.25 wt% potassium V-Ti-P catalyst prepared in Comparative Example 2.

X-ray diffraction pattern of the V-Ti-P catalyst prepared in Comparative Example 3.

Comparison of V-Ti-P performance

PROCESS FOR PREPARING MODIFIED V—TI—P CATALYSTS FOR SYNTHESIS OF 2,3-UNSATURATED CARBOXYLIC ACIDS

CROSS REFERENCE TO RELATED APPLICATIONS

This application is a divisional of U.S. patent application Ser. No. 14/509,517 filed on Oct. 8, 2014, now U.S. Publication Number 2015-0025272; which is a continuation application of U.S. patent application Ser. No. 13/234,323 filed on Sep. 16, 2011, now U.S. Pat. No. 8,883,672; the disclosures of which are incorporated herein by reference in its entirety.

FIELD OF THE INVENTION

The invention generally relates to the field of catalysis and, in particular, to mixed oxide catalysts modified with at least one alkali metal for the preparation of 2,3-unsaturated carboxylic acids.

BACKGROUND OF THE INVENTION 2,3-Unsaturated carboxylic acids and esters can be prepared from the reaction of a formaldehyde ($H_2CO$) source and a saturated carboxylic acid or ester containing one less carbon atom. Thus, acrylic and methacrylic acid derivatives can be prepared from the condensation of a formaldehyde source with acetic or propionic acid derivatives, respectively. The reaction produces one equivalent of water for each equivalent of carboxylic acid derivative reacted.

Although a number of catalysts have been proposed for this reaction, catalysts containing acidic vanadium and phosphorus oxides are among the most efficient, especially when a third component such as titanium or silicon is present in the catalyst. Water, however, tends to inhibit the condensation reaction with these catalysts. The use of formalin—which typically contains about 37 weight percent formaldehyde in water—as a starting material, therefore, is less efficient. Methanol can also be an inhibitor for the condensation reaction, and, since formalin can also contain methanol, the efficiency can be further lowered. When a carboxylic acid is the reactant, the presence of methanol in formalin can create a mixture of acids and methyl esters. And when an ester is the reactant, the water in formalin can create a mixture of acids and esters.

Industrial grade aqueous formaldehyde contains about 55 weight percent formaldehyde. It is relatively inexpensive and, therefore, is an economical source of this reactant. Thus, there is a need in the art for catalysts that are capable of condensing formaldehyde with alkanoic acids or esters in the vapor phase and that are tolerant of water in the feedstock. Ideally, such catalysts would also provide a high conversion of formaldehyde along with a high selectivity to the acrylic product.

Vanadium-titanium-phosphorus (V—Ti—P) mixed oxides are the best known catalysts for generating acrylic acid from the condensation of formaldehyde and acetic acid. But the preparation of these catalysts can be dangerous and is not amenable to scale-up. Typically, the titanium component is incorporated into these catalysts by first hydrolyzing liquid titanium chloride. This step, unfortunately, generates large quantities of hydrochloric acid fumes. Thus, there is also a need in the art for methods of preparing V—Ti—P mixed oxide catalysts that are safer and more amenable to industrial production.

In addition to the use of an industrially relevant formaldehyde feed source and the elimination of titanium chloride from the catalyst preparation, there is a need to further improve the yield of formaldehyde to the acrylic product as compared to a vanadium-titanium-phosphorus (V—Ti—P) catalyst.

The present invention addresses these needs as well as others that will be apparent from the following description and claims.

SUMMARY OF THE INVENTION

In a first aspect, the present invention provides a catalyst composition comprising a mixed oxide of vanadium (V), titanium (Ti), phosphorus (P), and alkali metal (M). The titanium component of the catalyst composition is derived from a water-soluble, redox-active organo-titanium compound.

In a second aspect, the present invention provides a method for preparing a catalyst composition comprising a mixed oxide of vanadium (V), titanium (Ti), phosphorus (P), and alkali metal (M). The method comprises the steps of:

(a) providing an aqueous solution comprising a water-soluble, redox-active organo-titanium compound;

(b) adding a vanadium compound, a phosphorus compound, and an alkali metal compound to the aqueous titanium solution to form a mixture of catalyst components;

(c) heat-treating the mixture;

(d) removing water from the heat-treated mixture to obtain a solid residue comprising the catalyst components; and (e) calcining the solid residue at an elevated temperature in the presence of air to obtain the catalyst composition.

In a third aspect, the present invention provides a process for preparing a 2,3-unsaturated carboxylic acid. The process comprises the step of contacting a formaldehyde source with a carboxylic acid in the presence of a condensation catalyst under vapor-phase condensation conditions to obtain the 2,3-unsaturated carboxylic acid. The condensation catalyst comprises a mixed oxide of vanadium (V), titanium (Ti), phosphorus (P), and alkali metal (M). The titanium component of the condensation catalyst is derived from a water-soluble, redox-active organo-titanium compound.

DETAILED DESCRIPTION OF THE INVENTION

Figure 1:
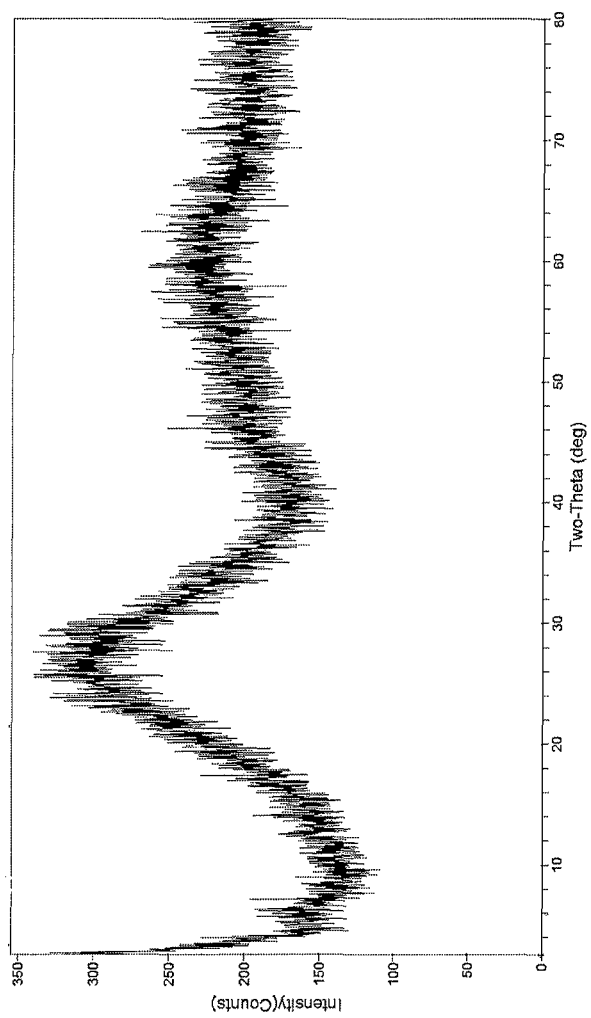
FIG. 1 is a graph showing the X-ray diffraction pattern of the catalyst of Example 1.

It has been surprisingly discovered that V—Ti—P-M mixed oxide catalysts can be prepared from a water-soluble, redox-active organo-titanium source. Employing such a titanium source can provide an inherently safer, and more practical and rapid route to V—Ti—P-M materials. In addition, it has been surprisingly discovered that the resulting catalysts can have a higher surface area and acidity, and can be more active for acrylic acid formation when an aqueous formaldehyde source and acetic acid are used as the feed.

Thus, in a first aspect, the present invention provides a catalyst composition comprising a mixed oxide of vanadium (V), titanium (Ti), phosphorus (P), and alkali metal (M). The titanium component of the catalyst composition is derived from a water-soluble, redox-active organo-titanium compound (sometimes referred to herein as simply "water-soluble titanium compound," "organo-titanium compound," or "titanium compound").

As used herein, the term "and/or," when used in a list of two or more items, means that any one of the listed items can be employed by itself, or any combination of two or more of the listed items can be employed. For example, if a composition is described as containing components A, B, and/or C, the composition can contain A alone; B alone; C alone; A and B in combination; A and C in combination; B and C in combination; or A, B, and C in combination.

It is to be understood that the mention of one or more process steps does not preclude the presence of additional process steps before or after the combined recited steps or intervening process steps between those steps expressly identified. Moreover, the lettering of process steps or ingredients is a convenient means for identifying discrete activities or ingredients and the recited lettering can be arranged in any sequence, unless otherwise indicated.

By "water-soluble," it is meant that the organo-titanium compound can dissolve in water at 20° C. and 1 atm absolute (101.325 kPa) to form a homogeneous solution of at least 1 weight percent of the organo-titanium compound. Preferably, the compound can dissolve in water to form a homogeneous solution of at least 25 weight percent. More preferably, the compound can dissolve in water to form a homogeneous solution of at least 40 weight percent.

By "redox-active," it is meant that the organic ligand of the organo-titanium compound is capable of reducing the oxidation state of vanadium from +5 to +4, +5 to +3, or +4 to +3. Alternatively, the organo-titanium compound is "redox-active" if the derivative of the organo-titanium compound, in the aqueous mixture used to make the catalyst, is capable of reducing the oxidation state of vanadium from +5 to +4, +5 to +3, or +4 to +3.

Examples of water-soluble, redox-active organo-titanium compounds include titanium lactates, titanium alkanolamines, and titanium acetylacetonates. Such compounds are commercially available, such as from Dorf Ketal under the tradename TYZOR®. Practical examples of such compounds include titanium(IV) bis(ammonium lactate)dihydroxide (TBALDH), titanium diethanolamine, titanium triethanolamine, and titanium acetylacetonate.

Examples of alkali metal include lithium, sodium, potassium, rubidium, and cesium. In one aspect, the alkali metal comprises potassium. In another aspect, the alkali metal comprises potassium and the water-soluble redox-active organo-titanium compound comprises titanium(IV) bis(ammonium lactate)dihydroxide.

The catalyst composition according to the present invention can have the general formula $VTi_aP_bM_cO_d$, wherein a=0.3 to 6.0, preferably 1.0 to 4.0; b=2.0 to 13.0, preferably 4.0 to 10.0; c=0.01 to 1.25, preferably 0.25 to 0.75; and d is the number of atoms required to satisfy the valences of the components other than oxygen.

The catalyst composition according to the present invention can be primarily amorphous in structure. One skilled in the art recognizes that an amorphous catalyst composition can have a small amount of crystalline structure caused, for example, by impurities. By "amorphous" or "primarily amorphous" it is meant that the catalyst composition contains less than 10 weight percent crystalline material. The percent crystallinity is calculated based on the integrated intensities of an X-Ray diffraction from the individual diffraction patterns with peaks of crystallite size greater than 30 Å defined as crystalline and peaks of crystallite size less than or equal to 30 Å defined as amorphous.

The catalyst composition of the invention can be supported on an oxide support. Suitable oxide supports include silica, alumina, titanium oxide, zirconium oxide, and titanium or zirconium pyrophosphates. Other oxide supports may be used provided that they are inert to the desired catalytic reaction. The supports should be physically robust and pre-shaped. The term "pre-shaped" is used in this context to mean that the shape of the final catalyst is essentially the same as the starting support. The pre-shaped oxides typically can have average particle diameter sizes ranging from about 0.1 millimeter (mm) to about 20 mm. They can be in any common form such as extrudates, compressed pellets, or bulk solid that has been pulverized to the desired mesh size. They may also be in a variety of shapes such as rods, stars, cylinders, spheres, or broken chunks.

In accordance with a second aspect of the invention, the catalyst composition according to the present invention can be prepared using the following general steps:

(a) providing an aqueous solution comprising the water-soluble, redox-active organo-titanium compound;

(b) adding a vanadium compound, a phosphorus compound, and an alkali metal compound to the aqueous titanium solution to form a mixture of catalyst components;

(c) heat-treating the mixture;

(d) removing water from the heat-treated mixture to obtain a solid residue comprising the catalyst components; and (e) calcining the solid residue at an elevated temperature in the presence of air to obtain the catalyst composition.

The aqueous solution containing the water-soluble titanium compound may be obtained directly from commercial sources or may be made by dissolving the titanium compound in water. The concentration of the aqueous titanium solution can vary over a wide range. For example, the solution can have a titanium compound concentration in the range of 25 to 75 wt %, or 30 to 70 wt %, or 50 to 60 wt %.

The mode of adding the vanadium compound, the phosphorus compound, and the alkali metal compound to the aqueous titanium solution is not particularly limiting. For example, the vanadium compound, the phosphorus compound, and/or the alkali metal compound may be blended together to form a physical mixture or a reaction product, before being added to the aqueous titanium solution. Alternatively, the vanadium compound, phosphorus compound and/or alkali metal compound may be added sequentially in any order or simultaneously to the aqueous titanium solution. Thus, as used herein, the expression "adding a vanadium compound, a phosphorus compound, and a alkali metal compound" can refer to the addition of the vanadium compound, the phosphorus compound, and the alkali metal compound separately and/or collectively as a physical mixture and/or as a reaction product of any combination of the compounds.

Similarly, the heat-treating step and the water-removing step may be conducted sequentially or simultaneously. For example, in the case of water removal by distillation or evaporation, the heat-treating step can take place during the distillation or evaporation.

The heat-treating step may be conducted over a wide temperature range, such as from above ambient up to 200° C. or higher. The purpose of the heat-treating step is to facilitate mixing and/or reaction among the catalyst precursors. Depending on the catalyst precursors and the temperature employed, the heat-treating step may be carried out from several minutes to hours or days.

The water-removal step may be accomplished in a number of ways. For example, as mentioned above, water may be removed by distillation or evaporation. Alternatively, as discussed in more detail below, the catalyst components can be precipitated out of solution by adding an anti-solvent to the mixture. The water can then be removed by decanting or filtration.

Following the water-removal step, which may include a subsequent drying step, the resulting solid residue may be crushed and sieved to obtain a desired particle size. The sieved catalyst particles can then be calcined in one or more stages in air prior to use. The calcining temperature is normally in the range of 200° C. to 800° C. Preferably, the calcining temperature ranges from 300° C. to 500° C. The calcining step is typically carried out for 1 to 10 hours, and preferably for 2 to 8 hours. Upon calcining, the mixed oxide catalyst according to the invention is formed.

In addition to the water-soluble titanium compounds mentioned above, the catalyst precursors may be ammonium salts, halides, oxyacids, oxyacid salts, hydroxides, or oxides of vanadium, titanium, phosphorus, and alkali metal.

The vanadium compound is preferably water soluble. Examples of such compounds include vanadium trichloride, vanadium(IV) sulfate oxide hydrate, and ammonium vanadate optionally treated with aqueous oxalic acid and/or lactic acid. Other water-soluble vanadium sources can also be used.

The phosphorus compound is also preferably water soluble. The phosphorus compound should be converted to phosphorus oxides when calcined. Such phosphorus compounds include phosphoric acid, phosphorous acid, and ammonium salts of these acids.

The alkali metal may contain lithium, sodium, potassium, rubidium, and/or cesium. The alkali metal compound is also preferably water soluble. Examples of such compounds include potassium nitrate, potassium nitrite, potassium sulfate, potassium carbonate, potassium phosphate, potassium metavanadate, lithium hydroxide, lithium carbonate, lithium nitrate, lithium phosphate, lithium sulfate, lithium pyrophosphate, rubidium carbonate, rubidium hydroxide, rubidium nitrate, sodium bisulfate, sodium bisulfite, sodium carbonate, sodium hydroxide, sodium lactate, sodium metabisulfite, sodium metavanadate, sodium nitrate, sodium nitrite, sodium phosphate, sodium pyrophosphate, sodium sulfate, cesium carbonate, cesium hydroxide, cesium nitrate, cesium orthovanadate, cesium sulfate, or mixtures thereof.

A reducing compound can be added to the reaction mixture to impart additional surface area to the resulting catalyst composition. Lactic acid is preferred for this purpose, but other compounds bearing bifunctional groups such as citric acid, glycolic acid, oxalic acid, ethylene glycol, butane diol, hexane diol, or pentane diol may also be used. Use of these surface area reagents is optional, but is generally preferred.

In one aspect of the invention the catalyst composition is prepared with the organo-titanium compound comprising titanium(IV) bis(ammonium lactate)dihydroxide and the alkali metal comprising potassium.

A practical example of a method for preparing the catalyst composition according to the invention includes mixing a 50 wt % aqueous solution of TBALDH with a solution of ammonium metavanadate, phosphoric acid, and potassium nitrate in water and, optionally, lactic acid; heating the mixture at 130° C. under agitation; removing water from the heat-treated mixture by distillation; and calcining the resulting residue at 300° C. and then at 450° C. in air.

Alternatively, according to another embodiment of the invention, the catalyst composition may be prepared as described above except that a water-miscible non-solubilizing solvent, or "anti-solvent," is added to the reaction/heat-treating vessel to precipitate out the majority of the catalyst components after the heat-treating step. In this way, energy intensive water removal by distillation can be avoided, and the catalyst composition may instead be collected by filtration followed by calcination. The anti-solvent may be polar compounds such as alcohols, ketones, aldehydes, ethers, or esters. Alcohols such as ethanol are preferred as the anti-solvent.

The catalyst composition according to the present invention can have the general formula $VTi_aP_bM_cO_d$, wherein a=0.3 to 6.0, preferably 1.0 to 4.0; b=2.0 to 13.0, preferably 4.0 to 10.0; c=0.01 to 1.25, preferably 0.25 to 0.75; and d is the number of atoms required to satisfy the valences of the components other than oxygen.

The catalyst composition of the invention can be supported on an oxide support. Suitable oxide supports include silica, alumina, titanium oxide, zirconium oxide, and titanium or zirconium pyrophosphates. Other oxide supports may be used provided that they are inert to the desired catalytic reaction. The supports should be physically robust and pre-shaped. The term "pre-shaped" is used in this context to mean that the shape of the final catalyst is essentially the same as the starting support. The pre-shaped oxides typically can have average particle diameter sizes ranging from about 0.1 millimeter (mm) to about 20 mm. They can be in any common form such as extrudates, compressed pellets, or bulk solid that has been pulverized to the desired mesh size. They may also be in a variety of shapes such as rods, stars, cylinders, spheres, or broken chunks. Many of these oxide supports are available commercially, and their use simplifies the preparation of the catalyst composition of the invention, although this is not a requirement of the invention. The pre-shaped support can be added to the mixture of catalyst components before the heat-treating step (c).

In supported embodiments, the titanium, the vanadium, and the alkali metal components can be loaded onto the support separately or together. A preferred technique is to dissolve the desired amount of ammonium vanadate, potassium nitrate, and oxalic acid or lactic acid in the aqueous TBALDH solution. This solution can be diluted if desired and then used to impregnate the oxide support using the incipient wetness technique. The impregnated support is then dried at about 110° C. The dried support containing the vanadium, titanium, and alkali metal is then impregnated with the desired amount of the aqueous solution of the phosphorus compound.

The order of impregnation normally is not critical. Co-impregnation of the support with vanadium, titanium, and alkali metal followed by impregnation with phosphorus after drying can be used as illustrated above.

Incipient wetness techniques can be used for all of the impregnations. If a higher loading is required, more solution than required for incipient wetness can be used followed by evaporation of the solvent. If desired, the solutions can be applied to the outer regions of the oxide support.

After the vanadium, titanium, phosphorus, and alkali metal components have been applied to the support, the catalyst can be calcined, for example, at about 450° C.

A reducing compound can be added to the reaction mixture to impart additional surface area to the resulting catalyst composition. Lactic acid is preferred for this purpose, but other compounds bearing bifunctional groups (i.e., bifunctional compounds) such as citric acid, glycolic acid, oxalic acid, ethylene glycol, butane diol, hexane diol, or pentane diol may also be used. Use of these surface area reagents is optional, but is generally preferred. In one aspect of the invention, the bifunctional compound can be added to the mixture of catalyst components before the heat-treating step (c). In one aspect of the invention, the bifunctional compound can comprise lactic acid.

The quaternary V—Ti—P-M catalyst composition disclosed herein is primarily amorphous, as determined by x-ray diffraction analysis. Interestingly, the invention V—Ti—P-M catalyst composition prepared with TBALDH, for example, produces acrylic acid in significantly higher yield (>15%) than unmodified V—Ti—P material prepared with TBALDH, and produces acrylic acid in significantly higher yield (>30%) than unmodified V—Ti—P material prepared with titanium chloride when a 55 weight percent aqueous formaldehyde feed is used. This result occurs even though all three catalysts are primarily amorphous materials.

The propensity for a water-soluble titanium compound, such as TBALDH, to form an active V—Ti—P-M catalyst comes as a surprise, since titanium sources other than $TiCl_4$ have been shown to produce inferior catalysts for acrylic acid production. See, for example, M. Ai, *Applied Catalysis*, Vol. 48, pp. 51-61 (1989). For example, when titanium dioxide is employed as a titanium precursor, the resulting material fails to generate acrylic acid from formaldehyde and acetic acid. It has been reported elsewhere that $TiO_2$ can form catalytically active materials for acrylate production (M. Abon et al., *J. Catalysis*, Vol. 156, pp. 28-36 (1995)); however, this result could not be reproduced.

Also unexpected is the fact that exogenous lactic acid is no longer required in the catalyst synthesis, for example, when TBALDH is used. When lactic acid is omitted from the catalyst preparation involving tetrachlorotitanium, the resulting material is highly crystalline, as determined by x-ray diffraction, but is relatively inactive toward acrylic acid synthesis. However, V—Ti—P-M materials prepared with TBALDH, for example, in the absence of lactic acid are amorphous and are considerably more active and selective. Avoiding lactic acid addition is appealing, since it minimizes the amount of steps in the catalyst synthesis and results in less organic material that must be com busted during air calcination.

One skilled in the art recognizes that the possession of a markedly acidic property is necessary for a catalyst to promote the condensation of formaldehyde and alkonoic acids or esters, and that a certain extent of basic property is also required. However, the ideal concentration of each property (i.e., number of acid sites and number of basic sites) is not known. There exist several techniques for determining the relative acidity and basicity of a heterogeneous catalyst, but it is hard to make comparisons across different techniques. One technique for measuring the concentration of acidic and basic sites on a solid surface is to perform temperature programmed desorption (TPD) experiments. For example, iso-propanol adsorption to a known quantity of catalyst sample followed by heating will form propylene if the material has acidic sites and acetone if basic sites are present. Multiple acidic or basic sites may be present in the sample, each with a distinct acid or base strength and each present in varying concentration. The amount of moles of each product (propylene or acetone) per gram of sample is a measure of the total concentration of each type of reactive site (acid or base). Therefore, the number of different acid or base sites may be inferred from the desorption curve in the TPD profile of each sample. Propylene, for example, will desorb from the varying acidic sites at different temperatures if more than one type of acid site is present in the sample. The magnitude of the maximum temperature (Tmax) of each propylene desorption curve is an indication of the corresponding acid site strength. In this case, higher temperature implies stronger acidic sites, or in other words, the reactant is bound more tightly to the surface at this site and requires more energy to initiate reaction and desorption of the product. Propylamine TPD experiments are also useful for acidity measurements. Desorption of physisorbed propylamine is a reflection of Lewis type acidity while desorption of propylene, which arises from propylamine chemisorption, is a measure of Brnsted acidity.

Alkali metal oxides typically possess basic characteristics and V—Ti—P oxides are predominantly acidic solids. Thus, it would be reasonable to expect that potassium inclusion in the V—Ti—P material would neutralize a portion of the acid sites on the catalyst surface. Indeed, the V—Ti—P catalyst possessing 2.5 wt. % potassium is considerably more basic, however it is also unexpectedly more acidic than the unmodified material. The formaldehyde conversion over the 2.5 wt. % potassium is, on average, more than 25% higher (i.e., percentage points higher, the simple difference in conversions) than that of the unmodified catalyst made with the same process; the acrylic acid yield is higher by about 15%. The formaldehyde conversion over the 2.5 wt. % potassium is, on average, more than 45% higher than that of the unmodified catalyst made by the process described in M. Ai, *Applied Catalysis*, Vol. 48, pp. 51-61 (1989) and JP 1989-068335A; the acrylic acid yield is higher by over 33%. This beneficial potassium effect comes as a surprise since higher potassium loadings do not necessarily produce more active V—Ti—P catalysts. Increasing the potassium concentration to 9.25 wt. % for example, affords a catalyst that converts formaldehyde in less than 25% and gives an acrylate yield of less than 20%.

Without being bound by any theory, applicants note that comparison of acid and base properties may not be sufficient to fully rationalize the improved performance of the 2.5 wt. % potassium catalyst since this catalyst has a higher than expected acid site content relative to the unmodified catalyst. The factors controlling the higher formaldehyde conversion could instead arise from defects in the catalyst imparted by the potassium promoter or from changes in the average vanadium oxidation state of the material.

In a third aspect, the present invention provides a process for preparing a 2,3-unsaturated carboxylic acid, such as acrylic acid or methacrylic acid. Reference to "carboxylic acid" in this context includes the corresponding carboxylic acid ester, such as acrylate and methacrylate.

The process of the invention comprises the step of contacting a formaldehyde source with a carboxylic acid in the presence of a condensation catalyst under vapor-phase condensation conditions to obtain the 2,3-unsaturated carboxylic acid. The condensation catalyst comprises a mixed oxide of vanadium (V), titanium (Ti), phosphorus (P), and alkali metal (M). The titanium component of the condensation catalyst is derived from a water-soluble, redox-active organo-titanium compound, as described herein.

The 2,3-unsaturated carboxylic acid can be prepared with good yield, conversion, and selectivity. By "yield" it is meant the (moles of product)/(moles of reactant fed)*100. For example, the % yield of acrylic acid from formaldehyde is the (moles of acrylic acid)/(moles of formaldehyde fed)*100. By "conversion" it is meant the (moles of reactant fed–moles of unreacted reactant)/(moles of reactant fed)*100. For example, the % formaldehyde conversion is (moles of formaldehyde fed–moles of unreacted formaldehyde)/(moles of formaldehyde fed)*100. By "selectivity" it is meant (moles of product)/(moles of reactant fed–moles of unreacted reactant)*100. For example, % selectivity to acrylic acid from formaldehyde is (moles of acrylic acid)/(moles of formaldehyde fed–moles of unreacted formaldehyde)*100. One skilled in the art recognizes that yield is also equal to conversion times selectivity. When comparing examples, such as, Example B has an 80% formaldehyde conversion and Example C has a 60% formaldehyde conversion, the formaldehyde conversion of Example B is said to be 20% higher than Example C. In other words, comparisons are simply the mathematical difference in the percentages from one example to another.

The formaldehyde source for use in the present invention is not particularly limiting. It can be anhydrous formaldehyde itself, 1,3,5-trioxane (sometimes referred to herein as simply "trioxane"), dimethoxymethane, or diacetoxymethane. Alternatively, the formaldehyde source may be an aqueous solution of formaldehyde. The aqueous formaldehyde solution can contain, for example, from 30 to 65 weight percent formaldehyde. Examples of such solutions include formalin (37 wt % formaldehyde) and industrial grade aqueous formaldehyde (55 wt % formaldehyde). The aqueous formaldehyde solution may be obtained commercially, by oxidation of methanol, or by blending water with trioxane, for example, in a molar ratio of approximately 4:1.

The carboxylic acid should have at least 2 hydrogen atoms in the position alpha to the carboxylic acid group. The carboxylic acid is preferably an aliphatic carboxylic acid having 2 to 4 carbon atoms. Acetic and propionic acids are preferred carboxylic acids. The most preferred carboxylic acid is acetic acid. The term "carboxylic acid" in this context includes the corresponding carboxylic acid ester, when formation of the 2,3-unsaturated carboxylic acid ester is desired. Examples of such carboxylic acid esters include acetate and propionate.

The description of the catalyst composition and the process for making the catalyst composition herein above, such as, for example, the description of vanadium, titanium, phosphorus, and alkali metal compounds, the catalyst formula, the alkali metals, the pre-shaped supports, the water removal step, and the bifunctional compound, apply to the process for preparing a 2,3-unsaturated carboxylic acid.

The molar ratio of the formaldehyde component to the carboxylic acid component may be from 0.1 to 10, preferably from 0.2 to 5, and more preferably from 0.2 to 2. The molar ratio of water to the formaldehyde component may be from 0 to 5, preferably from 0 to 3, and more preferably from 0 to 1.5.

The process can be operated at a temperature from 200° C. to 400° C., preferably from 225° C. to 375° C., and more preferably from 275° C. to 375° C.

The process can be run at a pressure from 0.1 to 10 bars absolute (bara), preferably from 0.5 to 5 bara, and more preferably from 1 to 1.5 bara.

In certain embodiments of the process of the invention, the liquid feed rate can range from 1.0 to 1000 mL/kg catalyst/minute, and preferably from 10 to 100 mL/kg catalyst/minute.

In other embodiments of the process of the invention, the reactants can be fed to the condensation reactor with oxygen along with an inert carrier gas such as nitrogen or oxygen-depleted air. Gases recycled from the process can be used. The inert gas component can be present at concentrations ranging from 0 to 90 mole % of the total feed, preferably from 25 to 85 mole %, and more preferably from 30 to 80 mole %. The concentration of the oxygen component can range from 0.5 to 6 mole %, preferably from 2 to 5 mole %, and more preferably from 3 to 4 mole %. Low levels of oxygen allow for coke to build up on the catalyst. On the other hand, high levels of oxygen can lead to excessive combustion of reactants and products.

Inhibitors such as hydroquinone may be added to the 2,3-unsaturated carboxylic acid product to minimize polymerization.

Listing of Non-Limiting Embodiments

Embodiment A is a catalyst composition comprising a mixed oxide of vanadium (V), titanium (Ti), phosphorus (P), and alkali metal (M) wherein the titanium component is derived from a water-soluble, redox-active organo-titanium compound.

The catalyst composition of Embodiment A which has the general formula $VTi_aP_bM_cO_d$, wherein a is a number from 0.3 to 6.0, b is a number from 2.0 to 13.0, c is a number from 0.01 to 1.25, and d is the number of atoms required to satisfy the valences of V, Ti, P, and M; or wherein a ranges from 1.0 to 4.0, b ranges from 4.0 to 10.0, and c ranges from 0.25 to 0.75.

The catalyst composition of Embodiment A or Embodiment A with one or more of the intervening features wherein the alkali metal is selected from at least one of lithium, sodium, potassium, rubidium, and cesium.

The catalyst composition of Embodiment A or Embodiment A with one or more of the intervening features wherein the organo-titanium compound comprises titanium(IV) bis(ammonium lactate)dihydroxide and the alkali metal comprises potassium.

The catalyst composition of Embodiment A or Embodiment A with one or more of the intervening features which further comprises a pre-shaped support.

The catalyst composition of Embodiment A or Embodiment A with one or more of the intervening features which further comprises a pre-shaped support, wherein the pre-shaped support comprises silica, alumina, titanium oxide, titanium pyrophosphate, zirconium oxide, or zirconium pyrophosphate.

The catalyst composition of Embodiment A or Embodiment A with one or more of the intervening features which further comprises a pre-shaped support, wherein the pre-shaped support has a particle size ranging from 0.1 mm to 20 mm.

Embodiment B is a method for preparing a catalyst composition comprising a mixed oxide of vanadium (V), titanium (Ti), phosphorus (P), and alkali metal (M). The method comprises the steps of:
  a. providing an aqueous solution comprising a water-soluble, redox-active organo-titanium compound;
  b. adding a vanadium compound, a phosphorus compound, and an alkali metal compound to the aqueous titanium solution to form a mixture of catalyst components;
  c. heat-treating the mixture;

d. removing water from the heat-treated mixture to obtain a solid residue comprising the catalyst components; and e. calcining the solid residue at an elevated temperature in the presence of air to obtain the catalyst composition.

The method of Embodiment B wherein the water removing step (d) comprises distillation or evaporation.

The method of Embodiment B wherein the water removing step (d) comprises adding an anti-solvent to the mixture to precipitate out the catalyst components and separating the precipitate from the liquid to obtain the solid residue.

The method of Embodiment B wherein the water removing step (d) comprises adding an anti-solvent to the mixture to precipitate out the catalyst components and separating the precipitate from the liquid to obtain the solid residue, and wherein the precipitate is separated from the liquid by filtration.

The method of Embodiment B wherein the water removing step (d) comprises adding an anti-solvent to the mixture to precipitate out the catalyst components and separating the precipitate from the liquid to obtain the solid residue, wherein the precipitate is separated from the liquid by filtration, and wherein the anti-solvent is a polar compound selected from alcohols, ketones, aldehydes, ethers, and esters; or wherein the anti-solvent is an alcohol.

The method of Embodiment B or Embodiment B with one or more of the intervening features wherein the catalyst composition has the general formula $VTi_aP_bM_cO_d$, wherein a is a number from 0.3 to 6.0, b is a number from 2.0 to 13.0, c is a number from 0.01 to 1.25, and d is the number of atoms required to satisfy the valences of V, Ti, P, and M; or wherein a ranges from 1.0 to 4.0, b ranges from 4.0 to 10.0, and c ranges from 0.25 to 0.75.

The method of Embodiment B or Embodiment B with one or more of the intervening features wherein the organo-titanium compound comprises titanium(IV) bis(ammonium lactate)dihydroxide and the alkali metal comprises potassium.

The method of Embodiment B or Embodiment B with one or more of the intervening features wherein the catalyst composition further comprises a pre-shaped support.

The method of Embodiment B or Embodiment B with one or more of the intervening features which further comprises a pre-shaped support, wherein the pre-shaped support comprises silica, alumina, titanium oxide, titanium pyrophosphate, zirconium oxide, or zirconium pyrophosphate.

The method of Embodiment B or Embodiment B with one or more of the intervening features which further comprises a pre-shaped support, wherein the pre-shaped support has a particle size ranging from 0.1 mm to 20 mm.

The method of Embodiment B or Embodiment B with one or more of the intervening features wherein the catalyst composition further comprises a pre-shaped support, and wherein the pre-shaped support is added to the mixture of catalyst components before the heat-treating step (c).

The method of Embodiment B or Embodiment B with one or more of the intervening features which further comprises adding a bifunctional compound to the mixture of catalyst components before the heat-treating step (c), wherein the bifunctional compound comprises citric acid, lactic acid, glycolic acid, oxalic acid, ethylene glycol, butane diol, pentane diol, or hexane diol; or wherein the bifunctional compound comprises lactic acid.

Embodiment C is a process for preparing a 2,3-unsaturated carboxylic acid. The process comprises the step of contacting a formaldehyde source with a carboxylic acid in the presence of a condensation catalyst under vapor-phase condensation conditions to obtain the 2,3-unsaturated carboxylic acid. The condensation catalyst comprises a mixed oxide of vanadium (V), titanium (Ti), phosphorus (P), and alkali metal (M). The titanium component of the condensation catalyst is derived from a water-soluble, redox-active organo-titanium compound.

The process of Embodiment C wherein the formaldehyde source comprises formaldehyde, 1,3,5-trioxane, dimethoxymethane, or diacetoxymethane and the carboxylic acid comprises acetic acid or propionic acid.

The process of Embodiment C or Embodiment C with one or more of the intervening features wherein the formaldehyde source comprises an aqueous solution of formaldehyde, 1,3,5-trioxane, dimethoxymethane, or diacetoxymethane and the carboxylic acid comprises acetic acid or propionic acid.

The process of Embodiment C or Embodiment C with one or more of the intervening features wherein the formaldehyde source comprises an aqueous solution of formaldehyde, 1,3,5-trioxane, dimethoxymethane, or diacetoxymethane and the carboxylic acid comprises acetic acid or propionic acid, and wherein the aqueous solution comprises from 30 to 65 weight percent formaldehyde.

The process of Embodiment C or Embodiment C with one or more of the intervening features wherein the alkali metal is selected from at least one of lithium, sodium, potassium, rubidium, and cesium.

The process of Embodiment C or Embodiment C with one or more of the intervening features wherein the organo-titanium compound comprises titanium(IV) bis(ammonium lactate)dihydroxide and the alkali metal comprises potassium.

The process of Embodiment C or Embodiment C with one or more of the intervening features wherein the catalyst composition further comprises a pre-shaped support.

The process of Embodiment C or Embodiment C with one or more of the intervening features which further comprises a pre-shaped support, wherein the pre-shaped support comprises silica, alumina, titanium oxide, titanium pyrophosphate, zirconium oxide, or zirconium pyrophosphate.

The process of Embodiment C or Embodiment C with one or more of the intervening features which further comprises a pre-shaped support, wherein the pre-shaped support has a particle size ranging from 0.1 mm to 20 mm.

This invention can be further illustrated by the following working examples, although it will be understood that these examples are included merely for purposes of illustration and are not intended to limit the scope of the invention. Unless otherwise indicated or the context indicates otherwise, all percentages are by weight.

EXAMPLES

Materials

D/L-Lactic acid (90 wt %), ammonium metavanadate (99+wt % $NH_4VO_3$), phosphoric acid (85 wt % $H_3PO_4$), titanium(IV) bis(ammonium lactate)dihydroxide (50 wt. % solution in water), tetrachlorotitanium (99 wt % $TiCl_4$), and potassium nitrate (KNOB) were purchased from commercial suppliers and used as received.

Abbreviations

XRD=Powder X-ray Diffraction, XRF=X-ray Fluorescence Spectroscopy, TPD=Temperature Programmed Desorption, SCCM=standard cubic centimeters per minute; MeOAc=methyl acetate, MeOH=methanol, MA=methyl acrylate, H2CO=formaldehyde; HOAc=acetic acid, HOPr=propionic acid, mmol=millimoles, prod=product, AA=acrylic acid, BSTFA=N,O-bis(trimethylsilyl)trifluoro-acetamide, and TMSCI=trimethylsilyl chloride.

XRD Measurements

All XRD measurements were performed on a Rigaku Miniflex X-Ray Diffraction Spectrometer using a Copper anode X-Ray tube operated at 30 kV and 15 mA. Diffraction patterns were collected from 2.5 degree two theta angle to 80 degree two theta angle with a sampling width of 0.02 degrees and a scan speed of 1.00 degrees/min.

Crystallite size was calculated based on the measurement of the full width half maximum for peaks in the diffraction pattern and use of the Scherrer equation (P. N. Scherrer, *Ges. Wiss. Gottingen, Math.—Phys.* Kl. 2, 96-100, 1918). Quantitative phase analysis was calculated using a refinement algorithm base on the Rietveld method (H. M. Rietveld, *J. Applied Crystallography* 21, 86-91 (1988)). Percent crystallinity was calculated based on integrated intensities from the individual diffraction patterns with peaks of crystallite size greater than 30 Å defined as crystalline and peaks of crystallite size less than or equal to 30A defined as amorphous (N. S. Murthy et al., *Polymers* 31, 996-1002 (1990)).

TPD Measurements

TPD determinations were conducted using a Mass Spectrometer attached to the outlet of a Micrometrics Autochem II 2920 analyzer. The determination of total acidity and total basicity using isopropanol as the probe molecule is performed as follows. Approximately 0.05 grams of sample is weighed into a quartz U tube which is placed in a ceramic furnace. The sample is subjected to a programmed temperature cycle that consists of a heat cycle to 450° C. under 10% oxygen in helium, a cooling step to 40° C. Isopropanol is dosed on the sample using the vapor generator of the Micromeritics Autochem 2920 Analyzer. The vapor generator operates by bubbling helium through a flask containing isopropanol at room temperature. The resulting "vapor-saturated" helium is transferred through a heated sample loop and injected over the sample. After saturating the surface of the sample, dry helium is passed over the sample to remove any physisorbed vapor. Then a final heating to ~450° C. at 20° C./min in a flowing stream of He at which time mass spectral data is collected from the gas flowing through the sample. The determination of Brnsted and Lewis acidity using ispropyl amine as the probe molecule is as follows. Approximately 0.05 grams of sample is weighed into a quartz U tube which is placed in a ceramic furnace. A controlled gas flow is sent through the tube. The sample is subjected to a programmed temperature cycle that consists of a heat cycle to 350° C. under He and a cooling step to 40° C. Isopropyl amine is dosed on the sample using the vapor generator of the Micromeritics Autochem 2920 Analyzer. The vapor generator operates by bubbling helium through a flask containing isopropyl amine at room temperature. The resulting "vapor-saturated" helium is transferred through a heated sample loop and injected over the sample. After saturating the surface of the sample, dry helium is passed over the sample to remove any physisorbed vapor. Then a final heating to ~500° C. at 20° C./min in a flowing stream of He at which time mass spectral data is collected from the gas flowing through the sample.

Gas Chromatography Measurements

Liquid product samples were collected over a measured time period, weighed, and analyzed by gas chromatography. Samples were weighed into a gas chromatography (GC) vial to a recorded weight of 0.1XXX (where X is the actual number shown on the balance). Then, a LEAP unit was used to robotically add 200 μL of internal standard (0.7325 g dodecane in 100 mL pyridine), followed by 1.0 mL of BSTFA (w/TMSCI). The vials were then placed on a heat plate at 80° C. for 30 minutes. To separate all components, each sample was injected on two columns running in parallel on one instrument, a Shimadzu 2010 gas chromatograph with an AOC-20 autosampler. Gas Chromatography measurements were used to quantify all components in the liquid product except formaldehyde.

Liquid Chromatography Measurements.

Quantitation of formaldehyde in the liquid product was performed using high performance liquid chromatography after liquid product samples were subjected to acid hydrolysis in aqueous 25% v/v $H_2SO_4$ at 80° C. for 30 minutes. The acid hydrolysate was reacted with dinitrophenylhydrazine then analyzed using a Phenomenex Luna C8 column using a 1:1 water:acetonitrile mobile phase under isocratic conditions. Separation and detection of the 2,4-dinitrophenylhydrazone derivative of formaldehyde was carried out using an Agilent 1100 HPLC system with a UV-Vis Detector monitoring at 360 nm. The formaldehyde concentration in the liquid product was calculated based on calibration using external standards prepared from formalin. The amount of formaldehyde fed to the reactor was calculated based upon the ratio of water to trioxane and the liquid feed flow rate.

Example 1

Preparation of an Amorphous V—Ti—P Catalyst with 2.5 wt % Potassium Loading and Reactor Screening with an Aqueous Liquid Feed 1. Preparation of 2.5 wt % K Modified V—Ti—P Catalyst The catalyst in this example was first prepared by suspending ammonium metavanadate (19.54 g) and potassium nitrate (7.22 g) in 218.38 g of a 50 wt % titanium(IV) bis(ammonium lactate)dihydroxide solution followed by addition of 200 mL of deionized water in a 1-L three-neck kettle reactor equipped with a distillation head and a mechanical stirrer. The beige suspension was stirred at 700 rpm for 10 min at room temperature, then 105.11 g of 85% phosphoric acid was added followed by a rinse with about 50 mL of water. There was an immediate color change to bright yellow and thickening of the mixture, then a change to green then pale green over 20 min. The stirred suspension was then heated to reflux (oil bath set at 130° C.) and about 175 mL of water was collected via distillation over five hours, leaving a pale green semi-solid with brown flecks. After cooling to room temperature, the resulting pale green semi-solid was scraped into a ceramic dish and calcined at 300° C. for 16 h in a muffle furnace in air to give black-green solids, which were sieved through an 8×14 mesh. The 8×14 meshed pellets were then calcined at 450° C. in a quartz tube furnace for 6 h with a 60 SCCM air flow to give pale green pellets. XRD analysis (FIG. 1) of this material reveals that it is 100% amorphous. The surface properties and bulk composition of the catalyst prepared in this example are summarized in Tables 1 and 2.

2. Preparation of Acrylic Acid

The vapor-phase condensation experiment with molar ratio 12 acetic acid/1 trioxane/4.09 water feed was performed at 325° C., 0.093 mL liquid feed/minute, and 49 SCCM $N_2$ and 21 SCCM air for twenty seven hours. The performance of the catalyst is summarized in Table 3. In Table 3, the term "Product, g" refers to the mass of the liquid products recovered. The term "Reactants fed, g" includes only those reactants fed as liquids to the reactor: trioxane, acetic acid, and water.

The condensation reaction of acetic acid, trioxane (the formaldehyde source), and water was performed in a 25-mm outer diameter (21 mm inner diameter) quartz reactor tube with length=79 cm (31 inches). Heat to the reactor was provided by an Applied Test Systems series 3210 three element electric furnace having a heated zone 50 cm (19.5 inches) in length. Liquid products were collected in a three-necked flask with a glycol chilled (0° C.) jacket. The three-necked flask was fitted to a water-cooled condenser, which was attached to a dry-ice condenser with a trap. The base of the receiver flask was fitted with a stopcock to allow for draining of the liquid products.

The quartz reactor had indentations 13 cm (5 inches) up from the base of the tube. The region of the reactor with the indentations was situated near the base of the heated section of the furnace. The reactor was also fitted with a thermowell that extended from the top of the reactor to about an inch below the indentations. The reactor was first loaded with quartz chips to about 8 inches in height above the indentations to allow the catalyst to be positioned in the middle of the three element furnace. The reactor was then loaded with a 5.0 g charge of catalyst. The thermocouple in the thermowell was placed near the center of the catalyst bed, approximately 1.5 inches up from the base of the catalyst bed. Sufficient quartz chips (about 2.5 inches) were added to the region above the catalyst charge to reach the top of the heated region of the furnace.

This example demonstrates that the catalyst containing 2.5 wt. % potassium produces acrylic acid from acetic acid and a 55 wt. % solution of formaldehyde in water. The average conversion, selectivity and yield from the twenty seven hour reaction are 80.5%, 86.5% and 69.5%, respectively. When compared to the performance of the unmodified V—Ti—P catalyst described in Comparative Example 1, the conversion and yield using the 2.5 wt % potassium catalyst are 25% higher and almost 15% higher, respectively. When compared to the performance of the unmodified V—Ti—P catalyst described in Comparative Example 3, the improvement in conversion and yield using the 2.5 wt % potassium catalyst are over 45% higher and over 30% higher, respectively.

Comparative Example 1

Preparation of an Amorphous V—Ti—P Catalyst and Reactor Screening with an Aqueous Liquid Feed 1. Preparation of V(IV) $H_3PO_4$ Solution The orange-beige ammonium metavanadate (19.53 g) was suspended in 50 mL of lactic acid and 200 mL of deionized water in a 500-mL single-necked round-bottomed flask. After heating at 70° C. for 1 hour, 85% orthophosphoric acid (105.2 g) was added to the clear blue vanadium solution at 70° C. over a 15-minute period to give a blue-green solution. Residual reactants were washed into the reaction flask with a minimal amount of water.

2. Preparation of V—Ti—P Catalyst

Figure 2:
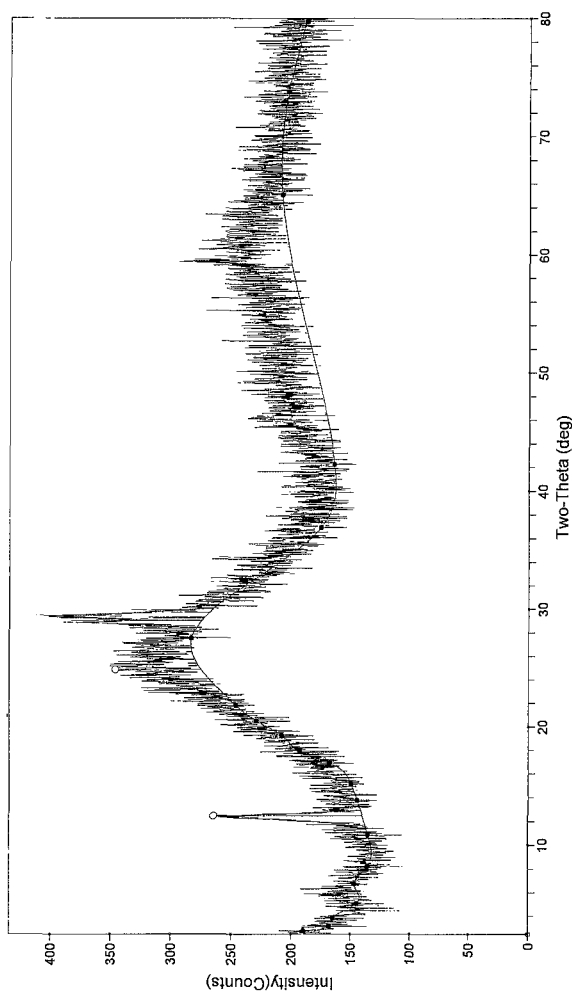
FIG. 2 is a graph showing the X-ray diffraction pattern of the catalyst of Comparative Example 1.

The 50 wt % titanium(IV) bis(ammonium lactate)dihydroxide solution (218.32 g) was added to a 1-L three-necked kettle reactor equipped with a condenser and a mechanical stirrer. The V/P solution from step 1 above was slowly poured into the Ti solution to give a blue suspension. The V/P flask was rinsed with 30 mL of water and the contents were added to the reaction flask. The mixture was then stirred at 700 rpm at 130° C. for 16 hours to give a blue to blue-green suspension. The water was then removed via distillation over 4 to 6 h (oil bath set at 130° C.), and the resulting damp pale green solid was transferred to a ceramic dish and heated in air at 300° C. for 16 hours in a muffle furnace. The resulting solid was then crushed and sieved through an 8×14 mesh. The 8×14 meshed material was then calcined for 6 hours at 450° C. in air (60 SCCM) in a quartz tube to give pale green irregularly shaped pellets. XRD analysis (FIG. 2) of this material indicated two small crystalline phases and an amorphous phase. The crystalline phases (hydrogen oxovanadium phosphate(V) hydrate and vanadium phosphorus oxide) were not completely resolved but were calculated to account for approximately 3% of the area of the diffraction pattern or corresponding to approximately 3% crystallinity in the sample; the catalyst is primarily amorphous. The surface properties and bulk composition of the catalyst prepared in this example are summarized in Tables 1 and 2.

3. Preparation of Acrylic Acid

The vapor-phase condensation experiment was conducted in the same manner as Example 1. The performance of the catalyst is summarized in Table 4.

The average conversion, selectivity and yield from the twenty seven hour reaction are 54.8%, 99.9% and 54.6%, respectively. This example demonstrates that the unmodified V—Ti—P catalyst prepared using the method of Example 1 has higher conversion and yield than the prior art catalyst of Comparative Example 3, but has lower conversion and yield than the potassium modified catalyst of Example 1.

Comparative Example 2

Figure 3:
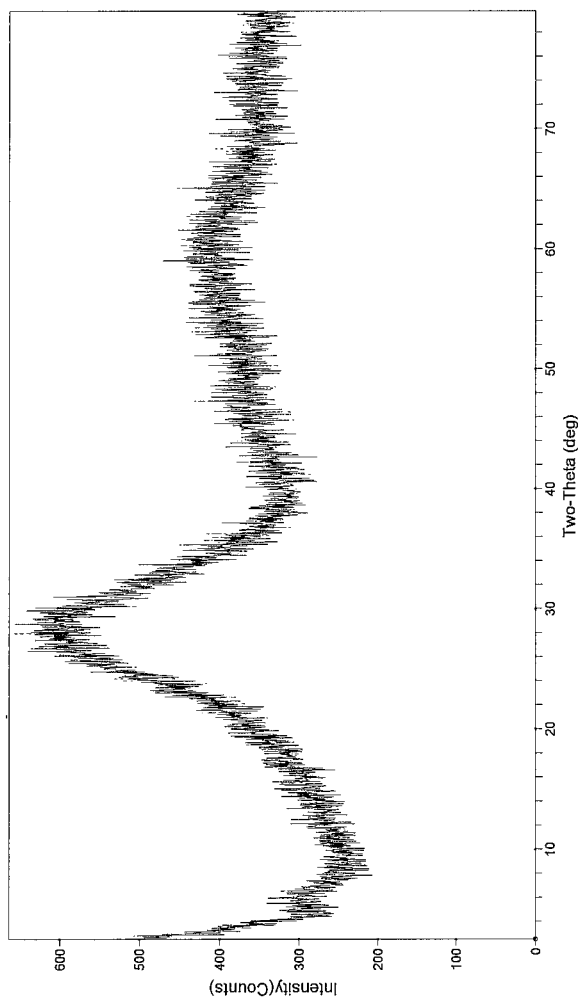
FIG. 3 is a graph showing the X-ray diffraction pattern of the catalyst of Comparative Example 2.

Preparation of a 9.5 wt % K Modified V—Ti—P Catalyst and Reactor Screening with an Aqueous Liquid Feed 1. Preparation of 9.5 wt % K Modified V—Ti—P Catalyst The catalyst in this example was prepared according to the procedure described in Example 1 except that 30.0 g of potassium nitrate was used during the initial mixing. XRD analysis (FIG. 3) of this material reveals that it is 100% amorphous. The surface properties and bulk composition of the catalyst prepared in this example are summarized in Tables 1 and 2.

2. Preparation of Acrylic Acid

The vapor-phase condensation experiment was carried out as described in Example 1. The performance of the catalyst is summarized in Table 5.

The average conversion, selectivity and yield from the twenty seven hour reaction are 18.2%, 101.4% and 18.1%, respectively. This example demonstrates that increasing the potassium concentration to 9.25% produces a modified V—Ti—P catalyst that is not as active as the 2.5 wt. % potassium catalyst of Example 1 nor as active as the unmodified catalyst of Comparative Examples 1 and 3.

Comparative Example 3

Preparation of Amorphous V—Ti—P Catalyst and Reactor Screening with an Aqueous Liquid Feed The catalyst in this example was prepared according to the methods described in M. Ai, *Applied Catalysis*, Vol. 48, pp. 51-61 (1989) and JP 1989-068335 A.

1. Ti(OH)$_4$ Gel Preparation

A 5-L three-necked round bottomed flask was charged with 300 mL of water ice and 300 mL of deionized water. The flask was fitted with a 125-mL addition funnel and vented to an aqueous saturated sodium bicarbonate solution. Tetrachlorotitanium (69.8 g) was then added slowly to the vigorously stirred water/ice mix. The reactor atmosphere was flushed into the scrubber solution with an air flow to remove gaseous HCl. The pH of the resulting colorless solution was between 0 and 1.

Once the solution warmed to room temperature, it was diluted with 2.5 L of deionized water and the pH was adjusted to between 10 and 11 by the addition of 500 mL of 5.0 M ammonium hydroxide. A bright white solid formed immediately. This material was filtered and washed with 2×1 L of water to give white pieces of a paste-like substance, which was air dried for up to five hours to give a white material with a gel-like consistency.

2. Preparation of V(IV) H₃PO₄ Solution

A V/P solution was prepared following the procedure of Comparative Example 1, step 1.

3. Preparation of V—Ti—P Catalyst

The hydroxide gel from step 1 above was suspended in 200 mL of water in a 1-L three-necked kettle reactor equipped with a condenser and mechanically stirred at 700 to 800 rpm long enough to obtain a homogeneous white suspension. The V/P solution from step 2 above was slowly poured into the gel suspension to give a blue suspension. The V/P flask was rinsed with 50 mL of water and the contents were added to the reaction flask. The mixture was then stirred at 700 to 800 rpm at 130° C. for 16 hours to give a blue to blue-green suspension.

Figure 4:
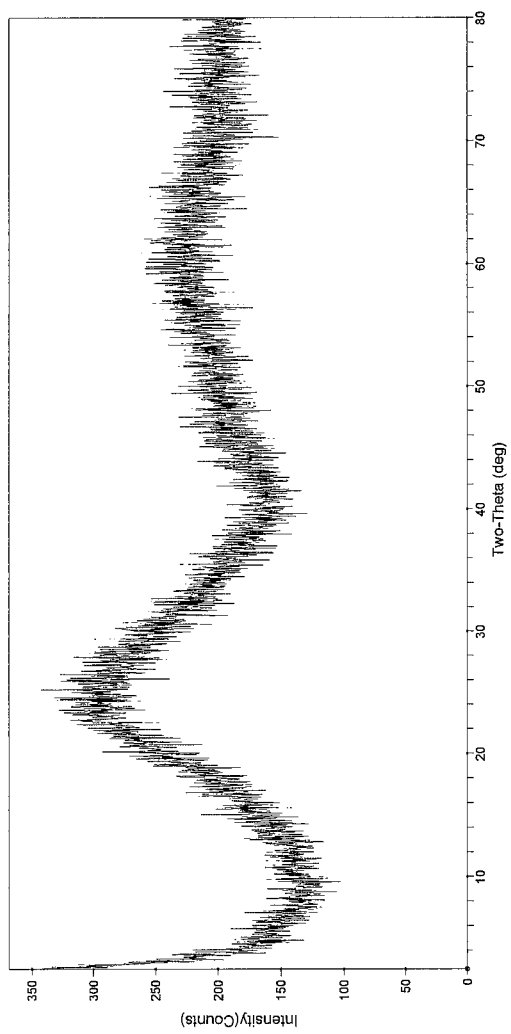
FIG. 4 is a graph showing the X-ray diffraction pattern of the V—Ti—P catalyst of Comparative Example 3.
Figure 5:
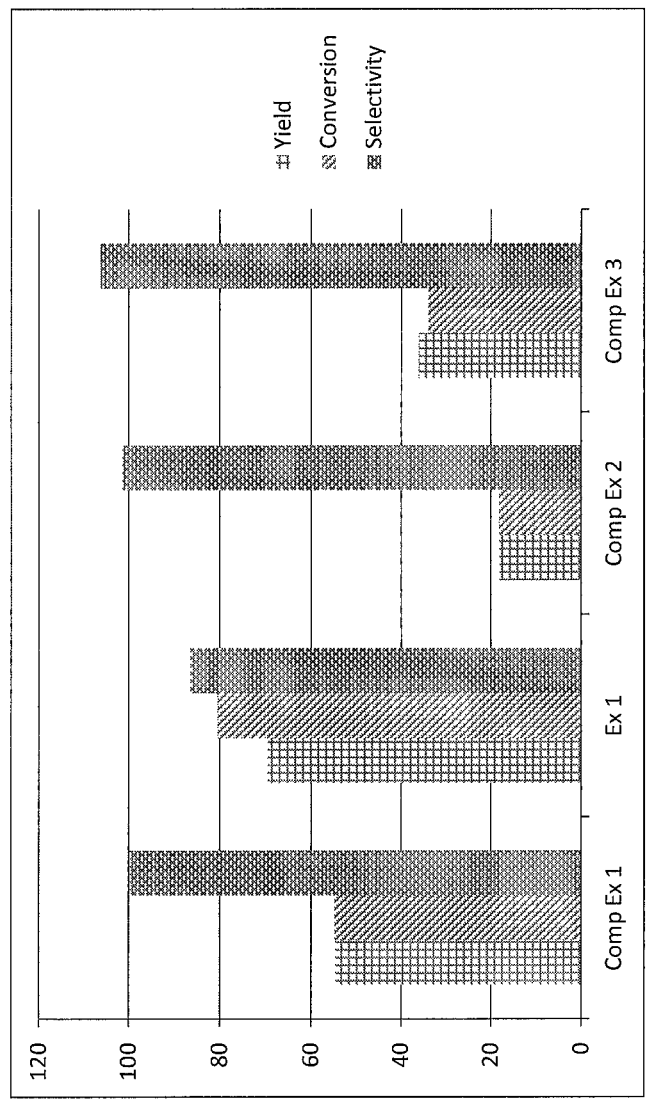
FIG. 5 is a graph showing comparison of V—Ti—P catalyst performance.

The water was then removed via distillation over 6 h (oil bath set at 130° C.) and the resulting damp pale green solid was transferred to a ceramic dish and heated in air at 300° C. for 16 hours in a muffle furnace. The resulting solid was then crushed and sieved through an 8×14 mesh. The 8×14 meshed material was then calcined for 6 hours at 450° C. in air (60 SCCM) in a quartz tube to give pale green irregularly shaped pellets. The surface properties and bulk composition of the catalyst prepared in this example are summarized in Tables 1 and 2. Powder x-ray diffraction analysis of the catalyst reveals that it is primarily amorphous (FIG. 4).

4. Preparation of Acrylic Acid

The vapor-phase condensation was performed as described in Example 1. The performance of the catalyst is summarized in Table 6.

The average conversion, selectivity and yield from the twenty seven hour reaction are 34.0%, 106.3% and 36.1%, respectively. This example demonstrates that the V—Ti—P catalyst prepared according to the prior art did not afford acrylic acid in as high a yield as the invention catalyst of Example 1 when an aqueous liquid feed was used. Even though the selectivity toward acrylic acid was similarly high and the reaction lifetime was comparable, the formaldehyde conversion was consistently lower than observed in Example 1 by more than 45%.

TABLE 1

Catalyst Characterization Data

| Example | Potassium Loading | BET Surface Area (m²/g) | Mole Ratio Bulk Composition (via XRF Measurement) |
|---|---|---|---|
| Ex. 1 | 2.5 wt. % | 65 | 1.00V:1.96Ti:5.14P:0.39K |
| Comp. Ex. 1 | 0 wt. % | 55 | 1.00V:1.92Ti:5.34P:0.00K |
| Comp. Ex. 2 | 9.25 wt. % | 44 | 1.00V:1.92Ti:5.1P:1.39K |
| Comp. Ex. 3 | 0 wt. % | 20 | 1.00V:1.81Ti:5.23P:0.00K |

TABLE 2

Catalyst Characterization Data

| | | iso-Propanol TPD | | n-Propylamine TPD | |
|---|---|---|---|---|---|
| Example | Potassium Loading | Total Acid Sites ($T_{max}$ desportion) | Total Base Sites ($T_{max}$ desportion) | Lewis Acid Sites ($T_{max}$ desportion) | Brønsted Acid Sites ($T_{max}$ desportion) |
| Ex. 1 | 2.5 wt. % | 80.1 µmol/g (128° C.) | 7.3 µmol/g (107° C.) | 4.8 µmol/g (136° C.) | 34.4 µmol/g (316, 338° C.) |
| Comp. Ex. 1 | 0 wt. % | 70.6 µmol/g (125° C.) | 2.8 µmol/g (93° C.) | 13.6 µmol/g (115° C.) | 26.6 µmol/g (294° C.) |
| Comp. Ex. 2 | 9.25 wt. % | 28.4 µmol/g (102, 187, 277° C.) | 5.9 µmol/g (107° C.) | 5.0 µmol/g (138, 311° C.) | 19.7 µmol/g (314, 359° C.) |
| Comp. Ex. 3 | 0 wt. % | 27.4 µmol/g (109° C.) | 0.6 µmol/g (96° C.) | 0.6 µmol/g (241° C.) | 7.8 µmol/g (287, 349° C.) |

TABLE 3

Performance Data for Example 1

| Example Number: | Example 1 | | |
|---|---|---|---|
| Catalyst descriptor: | V—Ti—P, 2.5 wt. % Potassium | | |
| Liquid feed molar composition | 12/1/4.09 HOAc/Trioxane/Water | | |
| Liquid feed flow rate (mL/min) | 0.089 | | |
| Nitrogen flow rate (SCCM) | 49 | | |
| Air flow rate (SCCM) | 21 | | |
| Time between samples (h) | 1.0 | 3.0 | 23 |
| Total run time (h) | 1.0 | 4.0 | 27 |
| Product, g | 4.80 | 16.48 | 128.64 |
| Reactants fed, g | 5.71 | 17.11 | 131.41 |
| GC/HPLC Results | | | |
| Formaldehyde, wt % | 1.23 | 1.73 | 2.12 |
| Acetone, wt % | 0.04 | 0.05 | 0.04 |
| MeOAc, wt % | 0.14 | 0.13 | 0.13 |
| Water, wt % | 16.32 | 16.42 | 15.73 |
| HOAc, wt % | 60.45 | 65.3 | 67.59 |
| Acrylic acid, wt % | 17.23 | 18.5 | 17.35 |
| HOPr, wt % | | | |
| Total knowns, wt % | 95.46 | 102.16 | 102.99 |
| Calculated Data | | | |
| mmol HOAc fed | 77.54 | 232.18 | 1783.32 |
| mmol HOAc in prod | 48.32 | 179.21 | 1447.92 |
| mmol HOAc consumed | 29.22 | 52.97 | 335.39 |
| mmol H2CO fed | 19.40 | 58.09 | 446.20 |
| mmol H2CO in product | 1.97 | 9.49 | 90.81 |
| mmol acrylic acid formed | 11.48 | 42.31 | 309.73 |
| mmol MeOAc formed | 0.09 | 0.28 | 2.27 |
| mmol acetone formed | 0.04 | 0.13 | 0.97 |
| mole ratio AA/acetone | 315.62 | 324.15 | 317.82 |
| mmol HOAc unaccounted for | 17.55 | 10.04 | 20.99 |

TABLE 3-continued

Performance Data for Example 1

Key Metrics

| | | | |
|---|---|---|---|
| % H2CO conversion | 89.87 | 83.66 | 79.65 |
| % selectivity to acrylic acid from H2CO | 65.98 | 87.21 | 87.28 |
| % yield acrylic acid from H2CO | 59.29 | 72.96 | 69.52 |
| % HOAc accountability | 77.36 | 95.68 | 98.82 |
| mole acrylic acid/kg-hr | 2.30 | 2.83 | 2.70 |

TABLE 4

Performance Data for Comparative Example 1

| | | | |
|---|---|---|---|
| Example Number: | Comparative Example 1 | | |
| Catalyst descriptor: | V—Ti—P, 0 wt. % Potassium | | |
| Liquid feed molar composition | 12/1/4.09 HOAc/Trioxane/Water | | |
| Liquid feed flow rate (mL/min) | 0.089 | | |
| Nitrogen flow rate (SCCM) | 49 | | |
| Air flow rate (SCCM) | 21 | | |
| Time between samples (h) | 1.0 | 3.0 | 23 |
| Total run time (h) | 1.0 | 4.0 | 27 |
| Product, g | 5.34 | 16.7 | 130.42 |
| Reactants fed, g | 5.84 | 17.08 | 131.7 |
| GC/HPLC Results | | | |
| Formaldehyde, wt % | 4.18 | 4.47 | 4.72 |
| Acetone, wt % | 0.073 | 0.096 | 0.096 |
| MeOAc, wt % | 0.184 | 0.195 | 0.206 |
| Water, wt % | 17.15 | 13.44 | 12.56 |
| HOAc, wt % | 66.14 | 70.01 | 69.44 |
| Acrylic acid, wt % | 12.84 | 13.68 | 13.57 |
| HOPr, wt % | 0.016 | 0.005 | 0.005 |
| Total knowns, wt % | 100.58 | 101.9 | 100.6 |
| Calculated Data | | | |
| mmol HOAc fed | 79.19 | 231.79 | 1787.04 |
| mmol HOAc in prod | 58.82 | 194.70 | 1508.14 |
| mmol HOAc consumed | 20.38 | 37.09 | 278.91 |
| mmol H2CO fed | 19.81 | 58.00 | 447.13 |
| mmol H2CO in product | 7.43 | 24.86 | 204.99 |
| mmol acrylic acid formed | 9.52 | 31.70 | 245.60 |
| mmol MeOAc formed | 0.13 | 0.44 | 3.63 |
| mmol acetone formed | 0.07 | 0.28 | 2.16 |
| mole ratio AA/acetone | 141.77 | 114.85 | 113.93 |
| mmol HOAc unaccounted for | 10.60 | 4.39 | 25.37 |
| Key Metrics | | | |
| % H2CO conversion | 62.49 | 57.14 | 54.15 |
| % selectivity to acrylic acid from H2CO | 76.85 | 95.67 | 101.43 |
| % yield acrylic acid from H2CO | 48.02 | 54.67 | 54.93 |
| % HOAc accountability | 86.62 | 98.10 | 98.58 |
| mole acrylic acid/kg-hr | 1.86 | 2.12 | 2.13 |

TABLE 5

Performance Data for Comparative Example 2

| | | | |
|---|---|---|---|
| Example Number: | Comparative Example 2 | | |
| Catalyst descriptor: | V—Ti—P, 9.25 wt. % Potassium | | |
| Liquid feed molar composition | 12/1/4.09 HOAc/Trioxane/Water | | |
| Liquid feed flow rate (mL/min) | 0.089 | | |
| Nitrogen flow rate (SCCM) | 49 | | |
| Air flow rate (SCCM) | 21 | | |
| Time between samples (h) | 1.0 | 3.0 | 23 |
| Total run time (h) | 1.0 | 4.0 | 27 |
| Product, g | 4.95 | 16.64 | 129.87 |
| Reactants fed, g | 5.71 | 17.14 | 131.41 |
| GC/HPLC Results | | | |
| Formaldehyde, wt % | 8.38 | 7.97 | 8.57 |
| Acetone, wt % | | | |
| MeOAc, wt % | 0.23 | 0.22 | 0.20 |
| Water, wt % | 15.06 | 13.79 | 13.34 |
| HOAc, wt % | 73.97 | 73.93 | 73.90 |
| Acrylic acid, wt % | 5.47 | 4.64 | 4.45 |
| HOPr, wt % | | | |
| Total knowns, wt % | 103.11 | 100.55 | 100.46 |
| Calculated Data | | | |
| mmol HOAc fed | 77.54 | 232.61 | 1783.32 |
| mmol HOAc in prod | 60.97 | 204.86 | 1598.23 |
| mmol HOAc consumed | 16.56 | 27.74 | 185.08 |
| mmol H2CO fed | 19.40 | 58.20 | 446.20 |
| mmol H2CO in product | 13.81 | 44.16 | 370.62 |
| mmol acrylic acid formed | 3.76 | 10.71 | 80.20 |
| mmol MeOAc formed | 0.15 | 0.49 | 3.51 |
| mmol acetone formed | 0.00 | 0.00 | 0.00 |
| mole ratio AA/acetone | n/a | n/a | n/a |
| mmol HOAc unaccounted for | 12.65 | 16.54 | 101.38 |
| Key Metrics | | | |
| % H2CO conversion | 28.80 | 24.12 | 16.94 |
| % selectivity to acrylic acid from H2CO | 67.26 | 76.33 | 106.12 |
| % yield acrylic acid from H2CO | 19.37 | 18.41 | 17.97 |
| % HOAc accountability | 83.68 | 92.89 | 94.32 |
| mole acrylic acid/kg-hr | 0.75 | 0.71 | 0.70 |

TABLE 6

Performance Data for Comparative Example 3

| | | | |
|---|---|---|---|
| | Comparative Example 3 | | |
| Catalyst Descriptor | V—Ti—P | | |
| Liquid feed molar ratio (HOAc/Trioxane/H2O) | 12/1/4.09 | | |
| Liquid feed flow rate (mL/min) | 0.089 | | |
| Nitrogen flow rate (SCCM) | 49 | | |
| Air flow rate (SCCM) | 21 | | |
| Time between samples (h) | 1.0 | 3.0 | 23 |
| Total reaction time (h) | 1.0 | 4.0 | 27 |
| Product, g | 5.42 | 16.72 | 130.91 |
| Reactants fed, g | 5.762 | 17.1 | 131.39 |
| GC/HPLC Results | | | |
| Formaldehyde, wt % | 6.61 | 6.87 | 6.78 |
| Acetone, wt % | 0.068 | 0.063 | 0.065 |
| MeOAc, wt % | | | |
| Water, wt % | 8.83 | 8.96 | 9.15 |
| HOAc, wt % | 72.59 | 73.16 | 72.15 |
| Acrylic acid, wt % | 8.68 | 8.35 | 8.98 |
| HOPr, wt % | | | |
| Total knowns, wt % | 96.85 | 97.4 | 97.12 |
| Key Metrics | | | |
| % H2CO conversion | 39.03 | 34.13 | 33.75 |
| % selectivity to acrylic acid from H2CO | 85.49 | 97.78 | 108.32 |
| % yield acrylic acid from H2CO | 33.37 | 33.37 | 36.56 |
| % HOAc accountability | 92.36 | 96.28 | 97.52 |
| mole acrylic acid/kg-hr | 1.29 | 1.29 | 1.42 |

The invention has been described in detail with particular reference to preferred embodiments thereof, but it will be understood that variations and modifications can be effected within the spirit and scope of the invention.

We claim:

1. A process for preparing a 2,3-unsaturated carboxylic acid, comprising:
    contacting a formaldehyde source with a carboxylic acid in the presence of a condensation catalyst under vapor-phase condensation conditions to obtain the 2,3-unsaturated carboxylic acid, wherein the condensation catalyst comprises a mixed oxide of vanadium (V), titanium (Ti), phosphorus (P), and alkali metal (M), and wherein the titanium component is derived from an organo-titanium compound, wherein the organo-titanium compound is titanium(IV) bis(ammonium lactate) dihydroxide.

2. The process according to claim 1, wherein the formaldehyde source is formaldehyde, 1,3,5-trioxane, dimethoxymethane, or diacetoxymethane and the carboxylic acid is acetic acid or propionic acid.

3. The process according to claim 1, wherein the formaldehyde source is an aqueous solution of formaldehyde, 1,3,5-trioxane, dimethoxymethane, or diacetoxymethane and the carboxylic acid is acetic acid or propionic acid.

4. The process according to claim 3, wherein the aqueous solution comprises from 30 to 65 weight percent of formaldehyde.

5. The process according to claim 1, wherein the alkali metal is selected from at least one of lithium, sodium, potassium, rubidium, and cesium.

6. The process according to claim 1, wherein the alkali metal comprises potassium.

7. The process according to claim 1, wherein the catalyst composition further comprises a pre-shaped support.

\* \* \* \* \*